(12) United States Patent
Thatipelli

(10) Patent No.: US 9,060,806 B2
(45) Date of Patent: Jun. 23, 2015

(54) DEVICE AND METHOD FOR TREATING A CHRONIC TOTAL OCCLUSION

(71) Applicant: Mallik Thatipelli, Bakersfield, CA (US)

(72) Inventor: Mallik Thatipelli, Bakersfield, CA (US)

( * ) Notice: Subject to any disclaimer, the term of this patent is extended or adjusted under 35 U.S.C. 154(b) by 50 days.

(21) Appl. No.: 13/801,228

(22) Filed: Mar. 13, 2013

(65) Prior Publication Data

US 2014/0277004 A1    Sep. 18, 2014

(51) Int. Cl.
  *A61B 17/50*    (2006.01)
  *A61B 17/3207*    (2006.01)
  *A61B 17/22*    (2006.01)

(52) U.S. Cl.
  CPC .......... *A61B 17/50* (2013.01); *A61B 17/320758* (2013.01); *A61B 2017/22068* (2013.01); *A61B 2017/22094* (2013.01); *A61B 2017/320733* (2013.01); *A61B 2017/320775* (2013.01)

(58) Field of Classification Search
  CPC .............. A61B 2017/32075; A61B 2017/3207
  USPC .......................... 606/159, 127, 128, 113, 114
  See application file for complete search history.

(56) References Cited

U.S. PATENT DOCUMENTS

| | | |
|---|---|---|
| 6,599,304 B1 | 7/2003 | Selmon |
| 7,763,012 B2 | 7/2010 | Petrick |
| 8,021,330 B2 | 9/2011 | McAndrew |
| 8,062,316 B2 | 11/2011 | Patel |
| 8,241,315 B2 | 8/2012 | Jenson |
| 8,361,094 B2 | 1/2013 | To et al. |
| 8,556,926 B2 | 10/2013 | Duerig |
| 2002/0128677 A1 | 9/2002 | Duerig |
| 2005/0038462 A1* | 2/2005 | Lubock et al. ................ 606/167 |
| 2005/0171572 A1* | 8/2005 | Martinez ....................... 606/200 |
| 2005/0216044 A1 | 9/2005 | Hong |
| 2006/0074442 A1* | 4/2006 | Noriega et al. ............... 606/159 |
| 2007/0083193 A1 | 4/2007 | Werneth |
| 2008/0281323 A1* | 11/2008 | Burbank et al. ................ 606/45 |
| 2009/0270714 A1 | 10/2009 | Duffy |
| 2010/0082051 A1 | 4/2010 | Thorpe et al. |
| 2010/0168557 A1 | 7/2010 | Deno |
| 2011/0022045 A1 | 1/2011 | Cao |
| 2012/0253186 A1* | 10/2012 | Simpson et al. ............. 600/426 |
| 2012/0283565 A1 | 11/2012 | Richter |
| 2014/0277009 A1 | 9/2014 | Thatipelli |

OTHER PUBLICATIONS

U.S. Appl. No. 11/090,435, filed Mar. 25, 2005, Hong.
U.S. Appl. No. 11/438,678, filed May 22, 2006, Werneth et al.

(Continued)

*Primary Examiner* — Todd Manahan
*Assistant Examiner* — Casey B Lewis
(74) *Attorney, Agent, or Firm* — Wilson Sonsini Goodrich & Rosati

(57) ABSTRACT

A device and method for opening blood vessel blockages, such as chronic total occlusions, is disclosed. The device has a main body and motor unit. The main body has an inner tubular member disposed inside an outer tubular member. The inner tubular member is reinforced with hydrophilic polymer coated wires, which are drawn out into two pairs of loops at the distal end of the device. The motor unit also has an inner tubular member disposed within an outer tubular member. The motor unit is used to create torque to rotate the main body having the pairs of loops. When torque transmitted to main body, the device spins. As the device is advanced through a blood vessel, the rotating loops penetrate and break down the occlusion, and recanalizes the blood vessel. Then device is then exchanged over a guidewire and further therapeutic interventions can be performed to improve blood flow.

13 Claims, 16 Drawing Sheets

(56) References Cited

OTHER PUBLICATIONS

U.S. Appl. No. 12/108,921, filed Apr. 24, 2008, Duffy et al.
U.S. Appl. No. 12/346,592, filed Dec. 30, 2008, Deno et al.
U.S. Appl. No. 12/893,707, filed Sep. 29, 2010, Cao et al.
U.S. Appl. No. 13/553,659, filed Jul. 19, 2012, Richter.
International search report and written opinion dated Jun. 20, 2014 for PCT/US2014/020607.

* cited by examiner

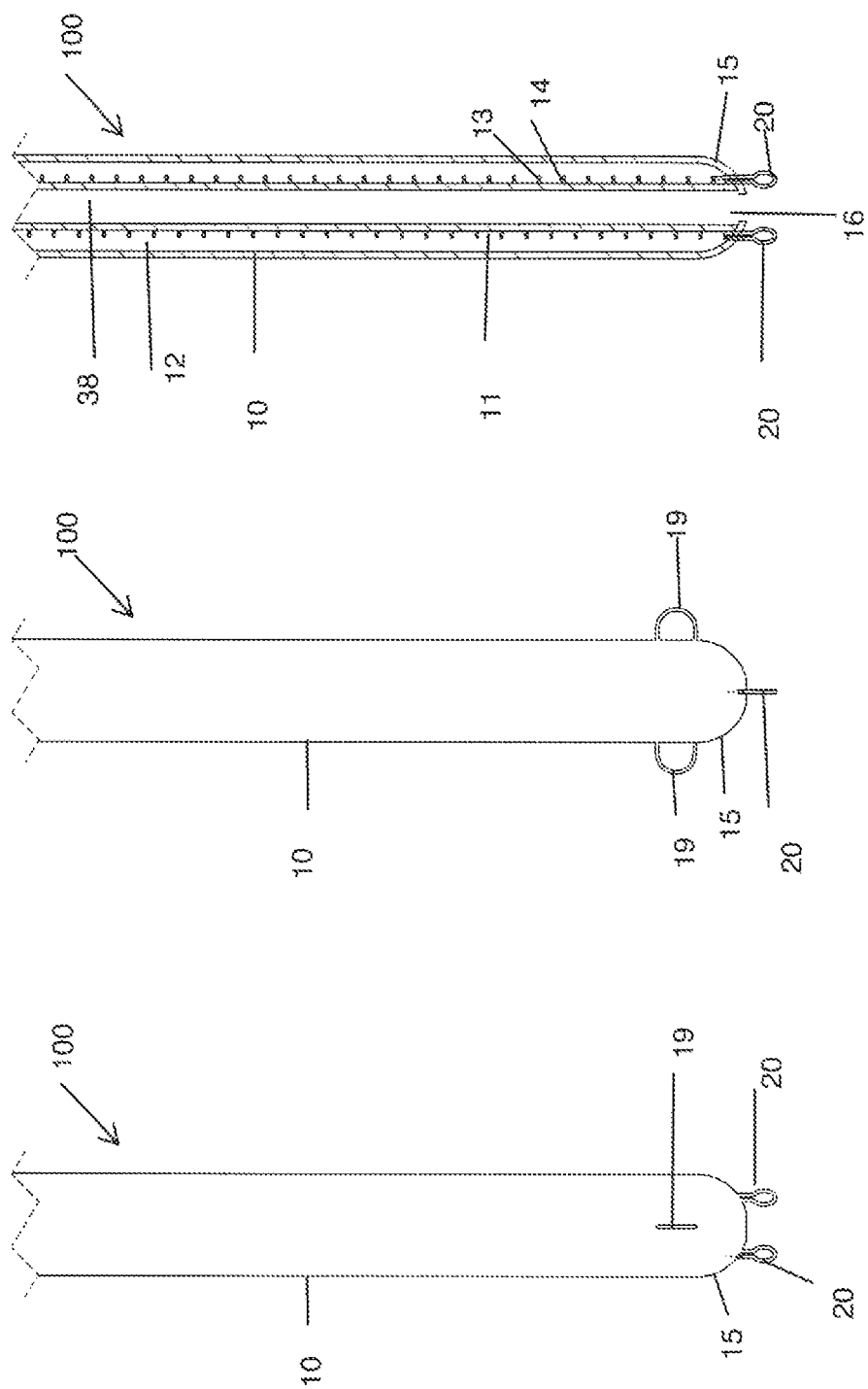

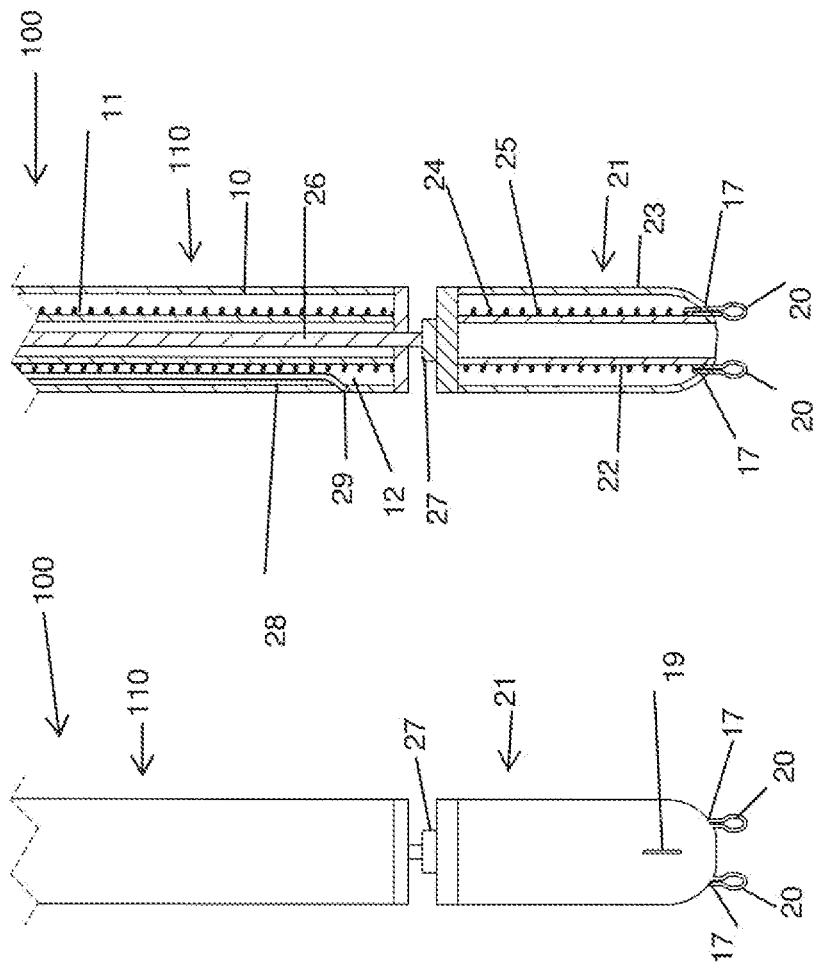
Fig. 3A
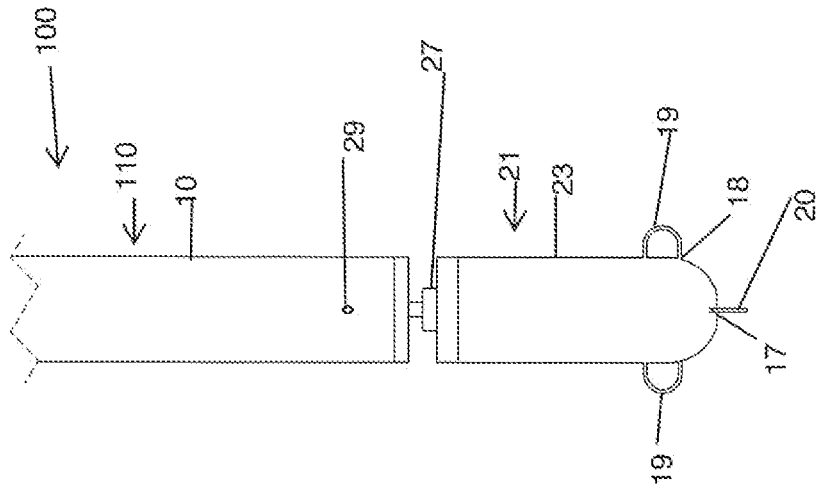
Fig. 3B
Fig. 3C

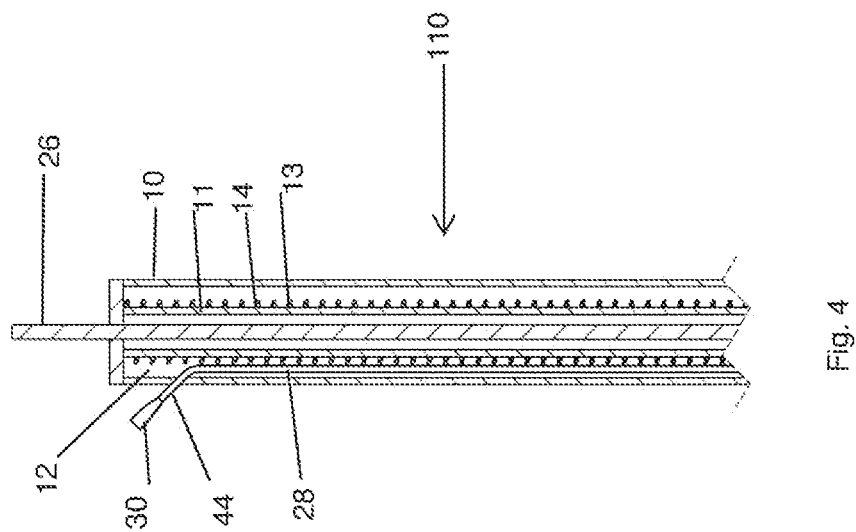

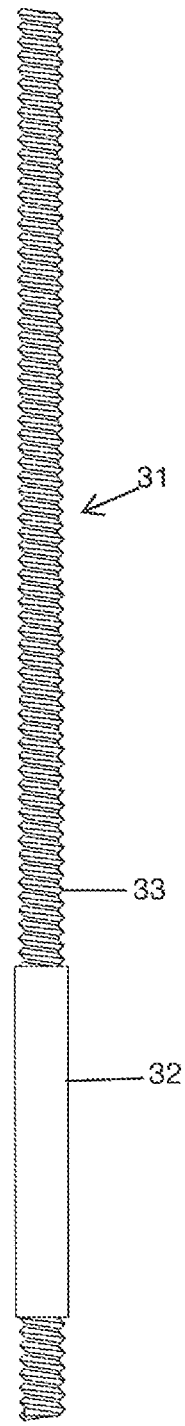
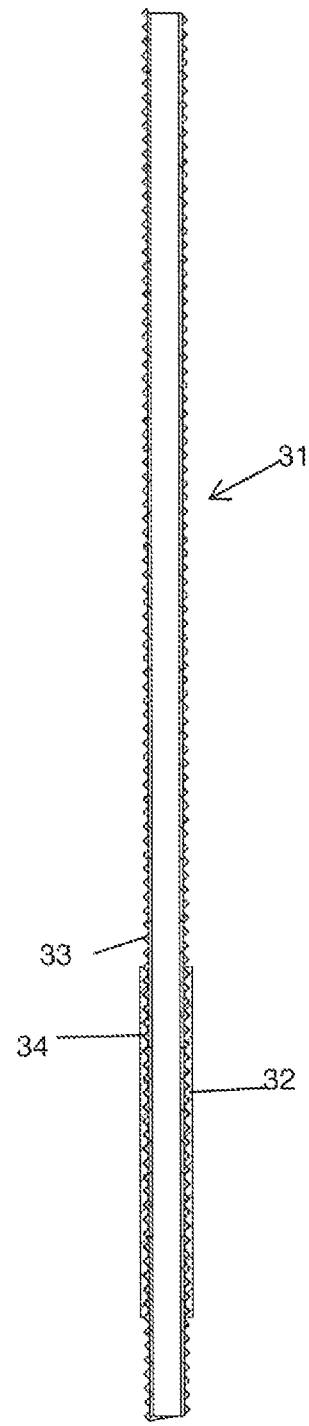
Fig. 7B                    Fig. 7A

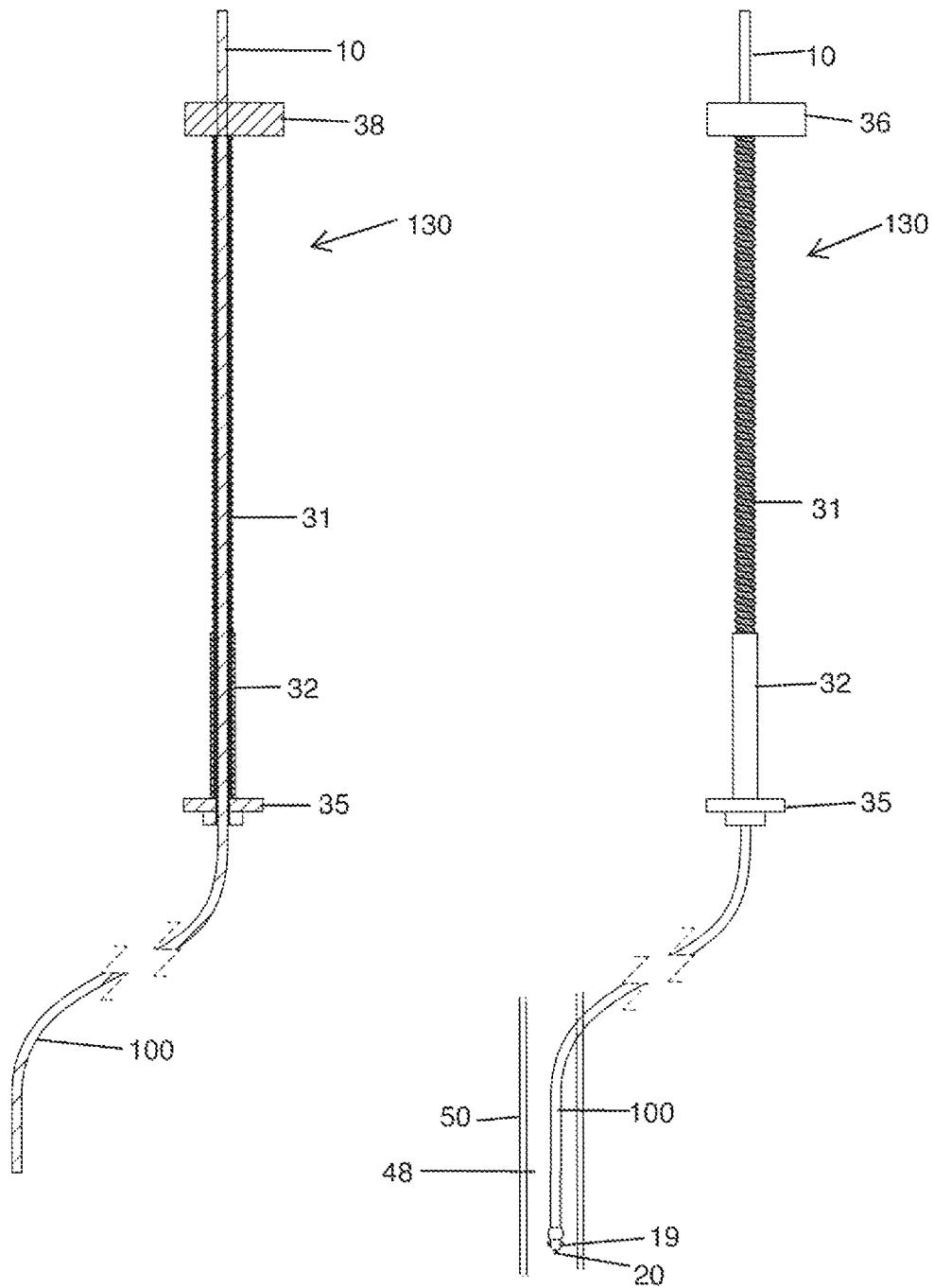

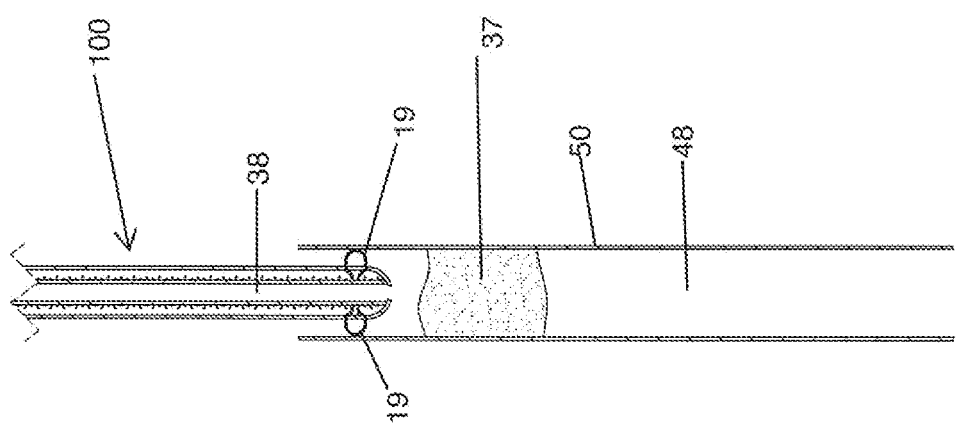

DEVICE AND METHOD FOR TREATING A CHRONIC TOTAL OCCLUSION

FIELD OF THE INVENTION

The present invention relates generally to a device and method for recanalizing blood vessels, and more particularly to a device and method for fracturing and opening chronic total occlusions.

BACKGROUND OF THE INVENTION

Chronic total occlusions (CTO) are vascular lesions that are totally occluded. These can occur anywhere in the human body such as coronary, carotid, visceral, iliac, femoral, and popliteal arteries and veins. Usually these lesions will develop over the course several months to years. Due to chronicity of their natural course, there usually will be an adequate amount time to for development of collateral vessels to supply blood to tissue. However these collateral vessels barely provide enough blood flow to keep the end organs alive and are inadequate to support the function of dependent organs.

Chronic total occlusions can have serious medical consequences depending on their location. For example, blockages located in coronary arteries can cause heart muscle damage and heart failure, whereas blockages located in femoral and popliteal arteries can cause leg ulcers and gangrene.

Chronic total occlusions per se are not "total occlusions", but rather contain several intrinsic nonfunctional narrow channels. Traditionally, hydrophilic coated guidewires are used to penetrate through one or more of these narrow channels to create a contiguous passage between open vessel segments proximal and distal to occlusion. This passage is subsequently dilated to accommodate therapeutic devices such as balloons or stents.

Various surgical and minimally invasive methods have been in vogue for many years for revascularization of CTOs. Surgical grafts, have been for many decades, designed to bypass blockages in coronary or peripheral vessels. Minimally invasive technologies include guidewires or CTO devices.

CTO lesions frequently contain extremely hard and calcified plaques, which makes them impenetrable. Guidewires, when used in CTOs, are sometimes risky as they can inadvertently damage or more ominously perforate the vessel wall. Often, the guidewire tip has insufficient support, and can buckle during an attempted penetration into the calcified plaque. The guidewire, when forced into a CTO, can also inadvertently be misdirected by the operator in an unintended direction, creating a dead end plane between the vessel wall and the plaque (i.e. a subintimal plane). If the guidewire fails to create successful passage through the CTO, the resulting subintimal tract prohibits the use of subsequent therapeutic devices such as a balloon, stent or atherectomy catheter. Another drawback in CTO devices includes shafts that are not robust enough to resist kinks when advanced inside of a CTO. Still another drawback is that the CTO device is not easily controlled, whereby the tip of the CTO device veers eccentrically away from the center of the blood vessel when the CTO device is pushed though the CTO. Due to these drawbacks, success rates with guidewires in CTO revascularization are marginal at best.

Several CTO technologies have been introduced in an attempt to overcome some of the difficulties faced when using guidewires and CTO devices to improve successful CTO penetration rates. In U.S. Pat. No. 6,599,304 Selmon et al, teach "an intravascular catheter system for the treatment of occluded blood vessels that includes tissue displacement or hinged expansion members that are movable from a closed to an open position. . . . A spreading or mechanical force may be thus applied to the vessel wall and occlusion so as to tear, fracture or otherwise disrupt the occlusion adjoining the vessel wall. This disruption of the occlusion may create a channel or passageway of sufficient size for the passage of guidewire or therapeutic catheter around or through at least a portion of the obstruction as part of an overall effort to restore regular circulatory function surrounding the occluded vascular region."

In U.S. Pat. No. 8,062,316, Patel et al. teach a CTO catheter with a novel rotating cutting head with helical blades at its distal end, the tip is lodged in a protective sheath. "Application of torque to an inner catheter or wire attached to the cutting head applies spin to the cutting head . . . . Depending on the angle and nature of the cutting head's protruding blades, the blades may either may be designed to simply cut through the occluding material, without actually dislodging the occluding material from the body lumen, or alternatively the blades may be designed to both cut through the occluding material, and severe its links to the body lumen, thereby dislodging the occluding material from the body lumen."

In U.S. patent application Ser. No. 11/090,435, Hong teaches a system for opening CTOs, by using a catheter having multiple channels. In addition, the catheter may have a bullet-shaped distal tip and/or torqueing grooves in the proximal and distal shaft, which will facilitate advancing catheter through CTO with manual torqueing action at the proximal end. Multiple channels running along the length of catheter are distensible and used to advance guidewires, balloons or stents into the lesion.

In U.S. Pat. No. 8,021,330, McAndrew teaches a novel balloon catheter with a "no-fold balloon at a distal end thereof that surrounds a distal portion of a guidewire shaft having a compliant shaft or tubular section for selectively gripping a guidewire there within." Upon inflation, the compliant soft section of the guidewire shaft locks onto the guidewire. "This provides the clinician a conjoined balloon catheter and guidewire ensemble that together may be pushed through a tight stenosis such as chronic total occlusion."

In U.S. patent application Ser. No. 12/108,921, Duffy et al. teach a visualization and treatment system for treating CTO. The system includes an elongated member configured to be tracked to the chronic total occlusion. The elongated member has a transducer located at its distal end. Acoustically activated material will be packed at the distal end of elongated member. The system also includes an external imaging system constructed and arranged to create an image of the chronic total occlusion. The external imaging system may also be configured to generate ultrasonic energy waves which in turn vibrate the acoustically activated material located at the distal end of the elongated member. These vibrations in turn produce mechanical energy that may be used to penetrate and cross CTO.

In U.S. patent Ser. No. 13/553,659, Richter teaches an apparatus and method for guided penetration of chronic total occlusion. This invention relates to an apparatus that facilitates accurate placement of guidewire and drilling tip within the blood vessel during recanalization of CTO. It comprises of an imaging system which can detect the lesion, vessel wall and guidewire tip in real-time. "Preferably, this apparatus also facilitates the penetration of a CTO or other obstruction in a vessel. The method of using the apparatus of the invention facilitates treatment of the occlusion and avoids or reduces complications and risks associated with treating the occlusion, such as perforation of walls of the vessel and creation of a false lumen."

In U.S. Pat. No. 7,763,012 Petrick et al. teach a catheter and method to cross CTOs. The catheter comprises of an elongated tubular member having a deflectable tip at the distal end. "The catheter is advanced to a region of interest in an artery proximal to a lesion. A control wire is operated to direct the deflectable tip toward the lesion. A guidewire is advanced through the lumen of the catheter and into the lesion to cross the lesion."

In U.S. Pat. No. 8,241,315 Jensen et al. teach an apparatus and method configured to penetrate occlusion while limiting inadvertent vessel damage. This device includes an elongated sheath and a stylet disposed within the elongated sheath. The stylet includes a lumen from proximal to distal ends which will allow passage of a guidewire after the occlusion is penetrated. In use, "the stylet can be moved distally such that the distal region of the stylet penetrates at least partially into the occlusion . . . . After the stylet has extended through the proximal cap, a guidewire can cross through the occlusion . . . . Then the recanalization assembly can be further advanced through the occlusion and the balloon placed near the distal cap and the stylet centered and passed across the distal cap."

Still, success rates with these new technologies are reportedly varied from 50-70% due to various factors including operator's experience. In addition, costs, cumbersomeness, need for complex preparation and lengthy training required for proper usage of these CTO devices can prohibit their widespread and cost efficient usage. Hence, despite these technological developments, there is still a great need for a simple, safe, easy-to-operate, efficient and cost effective CTO devices.

SUMMARY OF THE INVENTION

The present invention provides a device and method for treatment of vascular occlusions. It is an object of the invention to disrupt vascular occlusions or other blockages formed within blood vessels in order to provide pathways for the placement of guidewires, interventional devices and catheters as part of an overall effort to restore normal circulatory function having the advantages of a reinforced inner tube, easy controllability and a shape that prevents vessel damage but maximizes occlusion fracturing.

In a first embodiment of the present invention the vascular drilling device has a main body. The main body has several components that help direct and mechanically fracture the occlusion. The device has an outer tubular member. Inside of the outer tubular member is an inner tubular member interposed within. At the proximal end of the outer tubular member and inner tubular member is a distal cap that is sealed to both inner and outer tubular members. The distal cap preferably is a C-cup that does not have sharp edges to pierce vascular walls. At the distal end of the device is a plurality of distal end loops projecting from the distal end cap of the main body. A plurality of outer loops project from the outer tubular member proximal to the distal end loops. When the main body is advanced to the CTO, the operator spins the main body, either manually or mechanically. The loops on the distal end mechanically fracture the CTO in front of it. As the loops on the distal end advance forward into the CTO, the outer loops on the outer tubular member mechanically fracture the CTO nearer the vessel walls. Since all the loops have curved edges, even if the loops touch the vessel wall, it is unlikely that the device will pierce the vessel wall.

In one aspect of the invention, the inner tubular member is reinforced with one or more helically coiled wires. Preferably two helically coiled wires encircle the inner tubular member in a double helix fashion and are secured (by polymer glue or another securing substance) to the outer surface of the inner tubular member. The helically wrapped wire(s) allows flexibility of the main body to curve within the blood vessel lumen, and conform to the pathway of the blood vessel. Having wire(s) encircle the inner tubular member has the advantage of strengthening the shaft of the main body, such that the main body will not kink when curving along the pathway of the blood vessel. The coiled wires also have the advantage of improving steerability and pushability of the main body when advanced inside a diseased blood vessel or inside a hard fibrocalcific plaque of the occlusion.

In another aspect of the present invention, the device has an expandable material, such as a balloon, that envelops at least a portion of the main body and surrounds the outer tubular member of the main body. The distal end of the balloon is proximal to the outer loops. Configured in this way, when the balloon is inflated, the balloon presses against the vessel walls and centers the main body of the device to the center of the vessel. The use of an inflatable balloon therefore has the advantage of centering the main body so that mechanical fracturing of the occlusion occurs near the center of the vessel, thus preventing unwanted veering of the main body and distal end of the device into a vessel wall.

A distal end cap is sealed to the proximal ends of the inner and outer tubular members, The cap a central hole which creates an opening from the lumen of the inner tubular member out of the device so that a guidewire can be inserted within the lumen of the device and exit through this central hole. The guidewire can be used for further therapeutic procedures. Additionally, the distal end cap may have paracentral holes that allow a plurality of wire loops to project from the cap and fracture the occlusion.

In another embodiment, the CTO device has a motor unit to aid in rotating the main body and/or drilling tip. The motor unit has an electric motor to provide torque to the main body which spins the pairs of opposing loops to fracture the CTO and threaded inner and out motor unit tubular bodies. The motor unit is connected to the main body via these motor unit inner and outer tubular members. To aid in rotation of main body, the motor unit tubular members have helically threaded grooved surfaces so that when an electric motor turns the tubular members, rotational force can be translated into a linear force, which can drive the distal end of the device through a CTO. A locking screw may lock the motor unit to the main body.

In another embodiment of the invention, the main body is segmented into two units: a drilling unit and a stationary unit. The stationary unit can still be linearly inserted and refracted within the blood vessel, but does not rotate when the motor unit rotates. Thus the stationary unit is a rotationally stationary unit. Instead of the motor unit being coupled to the main body of the device directly, the motor unit is coupled to a torque transmitting member that is housed within the stationary unit. The stationary unit has a stationary unit outer tubular member and inner tubular member.

The torque transmitting member runs within the elongated lumen of the stationary unit inner tubular member and connects to the drilling unit via a coupling member. The drilling unit has the loops on its outer wall and distal end cap as previously described above.

An advantage of the main body separated into a stationary unit and a drilling unit is that only the small rotating portion of the main body (i.e. the drilling unit) rotates, instead of the entire main body rotating. A small rotating unit prevents unintended damage that may occur if the device rotates against a vessel wall, which would cause additive frictional forces that damage vessel walls.

In one aspect of the stationary unit and drilling unit embodiment, a guidewire tubule having a guidewire lumen is disposed between the inner and outer tubular members of the stationary unit, and a guidewire enters through a proximal hole and exits through a distal hole of the outer tubular member of the stationary unit. A guidewire can then be inserted through this lumen and left in the patient after the device is removed for use in further treatments.

In another aspect of the invention a motor sensor is incorporated into the distal end of the main body of the drilling unit, and a microprocessor is incorporated into the motor unit. The microprocessor acquires and analyzes data sent from the sensor about the motion of the drilling unit, and in turn sends commands to the motor unit that that operator is guiding. In this way, the speed and character of rotation of the distal end of the device or drilling unit can be more precisely controlled by the operator to suit CTO lesion characteristics.

A method of traversing a vascular occlusion using the above stated device is also disclosed. The steps involved in traversing the occlusion include first positioning the device such that the distal end is proximate to an occlusion. The distal end of the device is rotated so that the loops to fracture through the occlusion. As the device rotates, the operator advances the device through the occlusion. In one aspect of the method, a balloon enveloping a portion of the device the device is inflated to center the device within the blood vessel. The inflated balloon also presses the occlusion against the vessel wall to minimize the size of the occlusion. After successfully traversing the occlusion, a guidewire is passed through the guidewire lumen and the device exchanged out of the patient so that other procedures can take place after the device is removed from the vessel.

BRIEF DESCRIPTION OF THE DRAWINGS

FIG. 1A illustrates a front cross sectional view of a main body of a vascular drilling device.

FIG. 1B illustrates a front view of the device of FIG. 1A.

FIG. 1C illustrates a side view of the device of FIG. 1A.

FIG. 3A illustrates a front cross-sectional view of an alternative embodiment of distal end of a vascular drilling device.

FIG. 3B illustrates a front view of the device of FIG. 3A having a drilling unit and a rotationally stationary unit.

FIG. 3C illustrates a side view of the device of FIG. 3A.

FIG. 4 illustrates a side cross sectional view of a proximal end of the device of FIG. 3A.

FIG. 7A illustrates a side cross-sectional view of a motor unit inner tubular member interposed within a motor unit outer tubular member.

FIG. 7B illustrates a side view the motor unit inner tubular member interposed within a motor unit outer tubular member of 7A.

FIG. 8A illustrates a side view of an assembled motor unit over the main body of the CTO device inserted into a blood vessel.

FIG. 8B illustrates a cross sectional view of an assembled motor unit over the main body of a vascular drilling device.

FIG. 10A is a side cross sectional view of the device of FIG. 1A within a blood vessel before entering an occlusion.

DETAILED DESCRIPTION OF THE EMBODIMENTS

Figure 1E:
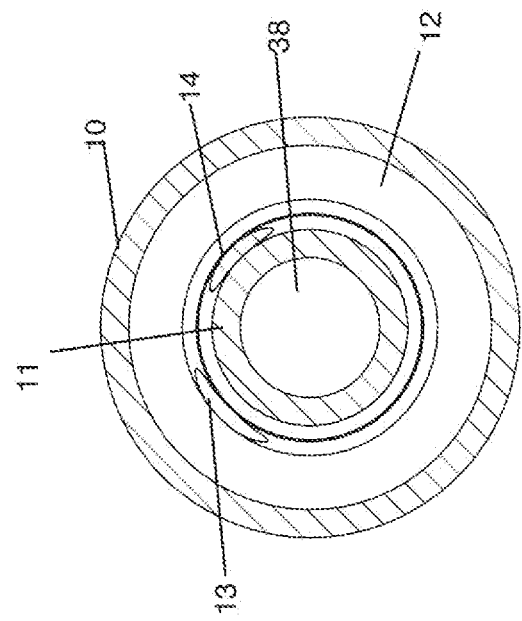
FIG. 1E illustrates a bottom cross-sectional view of the device of FIG. 1A.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Although the description of the invention is in the context of treatment of blood vessels, the invention may also be used in any other body passageways where it is deemed useful.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "having" and/or "has," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element(s) as illustrated in the Figures. It will be understood that relative terms are intended to encompass different orientations of the device in addition to the orientation depicted in the Figures.

The terms "distal" and "proximal" are used in the following description with respect to a position or direction relative to the treating clinician. "Distal" or "distally" describe a position distant from or in a direction away from the operator, and also refers to the tip of the CTO device closest to the occlusion. "Proximal" and "proximally" describe a position near or in a direction toward the operator and away from the occlusion.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As shown in FIGS. 1A-1E, the main body 100 comprises two tubular members: an inner tubular member 11, and an outer tubular member 10 disposed within the outer tubular member 10. The inner tubular member 11 has a lumen 38 where a guidewire can be passed though. Guidewires coated with a hydrophilic polymer are commonly used for crossing occlusive lesions inside of blood vessels. The polymer on the guidewire is activated in contact with water, which makes the guidewire surface highly lubricious and facilitates advancement of guidewires across narrow cracks and holes contained inside the atherosclerotic plaque of a CTO. The guidewire can be used to facilitate the drilling through the CTO.

Between the inner tubular member 11 and outer tubular member 10 exists an intertubular space 12 which is sealed on both ends of the main body 100 by a distal cap 15 which may be in the shape of a C-cup that seals the distal ends of both tubular members 11, 10. In a preferred embodiment, the inner tubular member 11 is at least 5 mm longer than the outer tubular member 10 such that the C-cup 15 has a depth of at least 5 mm. The curved C-cup prevents sharp edges from contacting a blood vessel which could possibly damaging the blood vessel wall 50.

The outer surface of the outer tubular member 10 may be coated with a highly lubricious hydrophilic polymer (such as polytetrafloroethylene or other hydrophilic polymer known to those having skill in the art) to facilitate free rotational and axial movement within the healthy or diseases blood vessels. The distal and proximal ends of the main body 100 and cap 15 may be sealed with a similar polymer. The main body 100 may be of a variety of lengths, but preferably, main bodies 100 between 90 cm and 130 cm are suitable for a majority of clinical applications.

The outer surface of the inner tubular member 11 is reinforced with one or more wires. These wires may be coated with a hydrophilic polymer. As shown in FIGS. 1A, 1E, 1F, 3A, 3B, and 4, the inner tubular member 11 is reinforced with two hydrophilic polymer coated wires 13, 14. These wires 13, 14 are wrapped around the inner tubular member 11 in a double helical fashion.

Figure 1D:
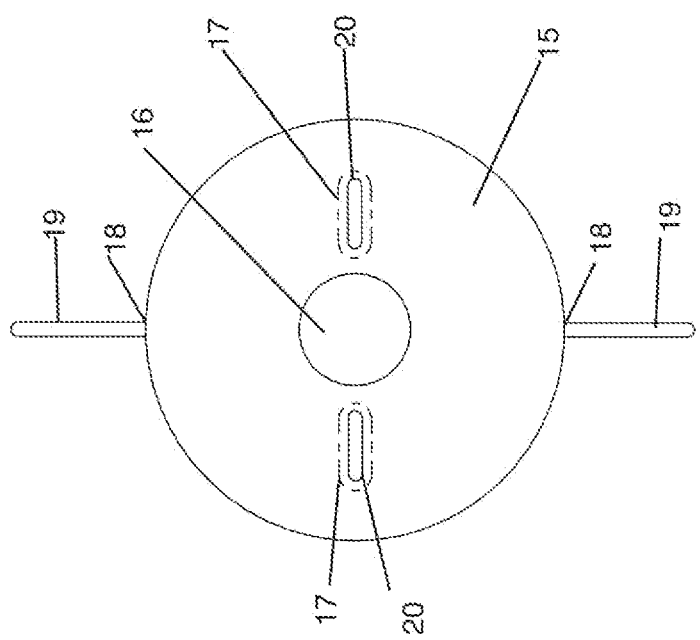
FIG. 1D illustrates a bottom view of the device of FIG. 1A.

In the embodiment illustrated in FIGS. 1A-1E, the distal cap 15 has a central hole 16 that is aligned with the inner tubular member 11 and provides an exit path for a guidewire to exit through the central lumen 38. Near the central hole 16 is a pair of paracentral holes 17 as illustrated in FIG. 1D. Each of the paracentral holes 17 is approximately 180 degrees from each other around the circumference of the cap 15 when viewed in cross section. Proximal to the paracentral holes 17 is a pair of outer tubular member holes 18. In one embodiment, the pair of outer tubular member holes 18 is proximally located between 0.5 cm and 2.0 cm from the most distal region of the distal cap 15. In a preferred embodiment, the pair of outer tubular member holes 18 is approximately 1.0 cm from the distal cap 15. In the embodiment illustrated in FIG. 1, each of the outer tubular member holes 18 is positioned approximately 180 degrees from each other, and the outer tubular member holes 18 are orthogonally positioned relative to to the paracentral holes 17. In a preferred embodiment, each of the outer tubular member holes 18 is approximately 4.0 mm to 5.0 mm away from each other along the long axis of the outer tubular member of the main body 100.

Each of the wires 13, 14 are helically coiled around the shaft of the inner tubular member 11. The wires 13, 14 are drawn out through the paracentral holes 17, 18 to form a distal end loops 20, and a pair of outer loops 19. The loops 18, 19 are secured to the holes 17, 18 with a spot fixing polymer. In some embodiments, the distal end loops 20 may be oriented slightly inward (not shown), toward the central axis. Presumably, this orientation will lessen the chances of vessel wall trauma caused by the distal loops 20 while the device is spinning.

This type of loop design and configuration where there is a distal pair of loops 20 pointed toward the occlusion, and outer loops 19 pointed in the direction of the vessel wall 50 is advantageous because as the device penetrates and advances through the CTO, the device will penetrate the CTO proximal cap at four different locations positioned approximately 90 degrees from each other at different depths of the CTO.

In a preferred embodiment, the main body of the device is approximately 5 mm in diameter at the level of the outer loops 19, which helps in keeping the distal end of the main body 100 in the centric part of the occlusion during device use. A device centrally positioned in the occlusion plaque has less chance of trauma to vessel walls and a higher chance of re-entry into the true lumen of the vessel located distal to the CTO. In contrast, a device whose distal end is positioned closer to the vessel wall has a higher chance of vessel trauma leading to dissection and/or perforation of the vessel wall. In addition, if the distal end of the device is disposed eccentrically and close to the vessel wall, its chances of re-entering the true lumen of the vessel is poor. If the device tip is closer to the vessel wall the tip may also create a subintimal dissection plane, which can advance within the vessel wall distal to the CTO, instead of the intended reentry into the true vessel lumen.

Figure 1F:
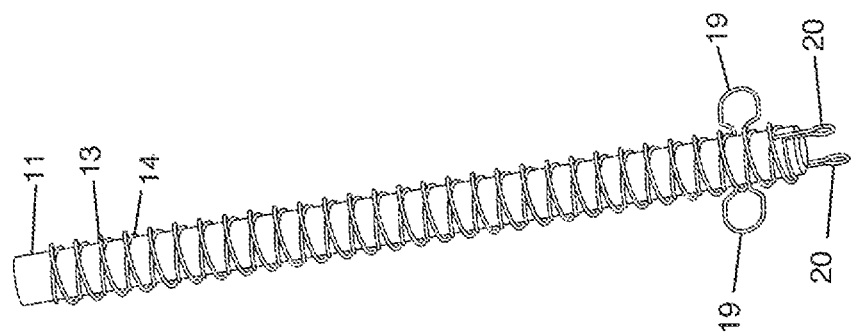
FIG. 1F illustrates a front view of the inner tubular member of the device of FIG. 1A.

FIG. 1F illustrates the inner tubular member 11 without the outer tubular member 10. Here, the wires 13, 14 can be seen in double helix fashion around the inner tubule member, and forming the outer loops 20 and distal loops 19 projecting from the inner tubular member 11. When assembled, the outer loops 19 project from the outer tubular member 10 and the distal loops project from the distal cap 15 as illustrated in FIGS. 1A-1E.

Figure 2B:
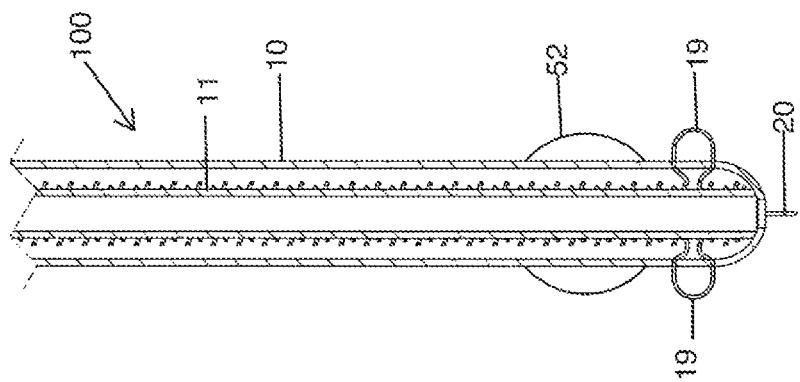
FIG. 2B illustrates a side view of the device of FIG. 1C having an inflatable balloon.
Figure 2A:
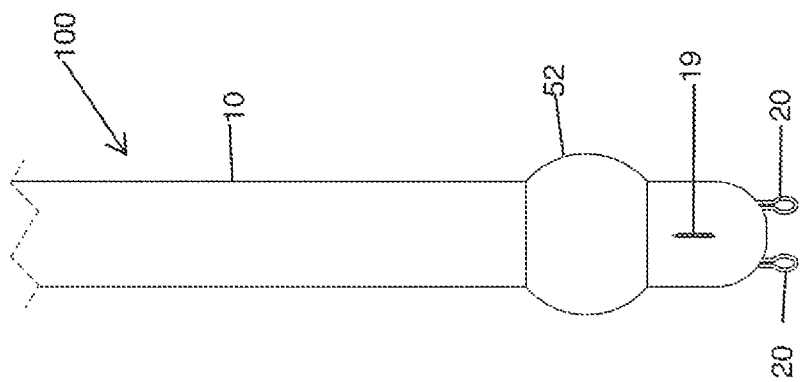
FIG. 2A illustrates a front cross sectional view of the device of FIG. 1B having an inflatable balloon.
Figure 3D:
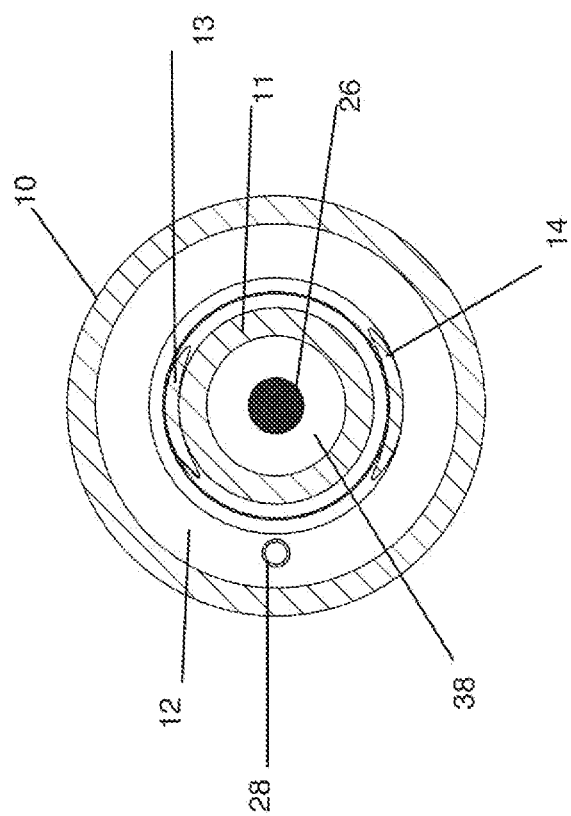
FIG. 3D illustrates a bottom cross-sectional view of the stationary unit of FIG. 3A.

In another embodiment of the device, a dilation balloon 52 envelops a portion of the main body 100 as depicted in FIGS. 2A and 2B. In a preferred embodiment, the balloon 52 is approximately 5.0 cm to 7.0 cm in length, between 5.0 mm and 6.0 mm in diameter, and made of a polyethylene material. The balloon 52 is positioned over the outer tubular member 10 around at approximately 1 cm proximal to the outer loops 19. In this embodiment, the intertubular space 12 between the outer tubular member 10 and inner tubular member 11 is used as infusion lumen. The balloon 52 communicates with the infusion lumen which extends to the proximal end of the main body. When inflated with infusion media, the balloon 52 repositions the distal end of the main body 100 toward a centric position inside the vessel, and also dilates the passage made by the device inside the CTO, thus facilitation stent placement.

FIGS. 3A-3D illustrate another embodiment of the main body 100 of the CTO device. The main body 100 is segmented into a stationary unit 110 and a drilling unit 21. The drilling unit 21 spins when torque is applied to it via a torque transmitting member 26 which runs lengthwise through the lumen 38 of the main body 100. The torque transmitting member 26 can be a solid or hollow wire, tube, or shaft, made from a variety of materials, such as stainless steel (SS 304) or similar compatible material. The torque transmitting member 26 is coupled to the drilling unit 21 via a coupler 27, which connects the drilling unit to the stationary unit 110, and forms the entire main body 100 of the CTO device. In one embodiment, the drilling unit 21 is approximately between 2.0 and 4.0 cm in length. In a preferred embodiment, the drilling unit 21 is approximately 3.0 cm in length. The drilling unit 21 has the features of the distal end of the embodiment illustrated in FIGS. 1A-1F. However, in the embodiment of the drilling unit 21 shown in FIGS. 3A-C, there is no distal end cap hole 16 to allow a guidewire to pass through the lumen 38 of the distal cap 15. The proximal end of the drilling unit 21 is covered with proximal cap 42 and the distal end of the stationary unit 110 is covered with a distal cap 40. The coupler 27 attaches to the proximal cap 42 on the drilling unit 21 to connect the stationary unit 110 to the drilling unit 21.

One advantage of the segmented main body 100 embodiment of FIGS. 3A-3C is that the drilling unit 21 spins independently of the stationary unit 110, which does not spin when the torque transmitting member 26 rotates. Since only the small drilling unit 21 spins, most of the main body 100 within the blood vessel remains rotationally stationary, and thus does not produce any frictional forces against inner wall of the blood vessel. Hence the operator will have a better control over the exact location of the drilling action of the device. This segmented main body 100 increases the safety of the device and prevents unwanted force on non-occluded areas of the blood vessel.

To accommodate a guidewire in this embodiment, a guidewire tubular member 44 is located within the intertubular space 12 of the stationary unit 110, which has a guidewire lumen 28. A guidewire 39 can be passed through the guidewire lumen 28 and exits the stationary unit 110 at guidewire exit hole 29, so the guidewire can be used in later procedures. In one embodiment, the exit hole 29 is located between 0.5 and 5.0 cm proximal to the distal end stationary unit 110. In a preferred embodiment, the exit hole 29 is located approximately 1.0 cm proximal to the distal end of the stationary unit 110. The helically coiled wires 13, 14 are helically wrapped and secured around the stationary unit's inner tubular member 11, and a second pair of wires 24, 25 is wrapped around and secured to the inner tubular member 11 of the drilling unit 21. In a preferred embodiment, a first wire 24 is helically wrapped around the inner tubular member 11 and forms two of the four loops 19, 20 (projecting from one outer tubular member hole 18, and one paracentral distal cap hole 17). A second wire 25 is helically wrapped around the inner tubular member 11 and forms the other two of four loops (projecting from the opposing outer tubular member hole 18, and the opposing paracentral distal cap hole 17). The loops 19, 20 on the distal unit 21 are brought out through the holes 17, 18, and spot fixed as previously described in FIGS. 1A-1E.

FIG. 4 illustrates the proximal end of the stationary unit 110 of FIG. 3. The torque transmitting member 26 exits the proximal end of the stationary 110 to attach to a motor unit, which applies torque to the torque transmitting member 26. The guidewire tubular member 44 has a guidewire entrance hole 30 for insertion of a guidewire into the stationary unit 110.

Figure 5B:
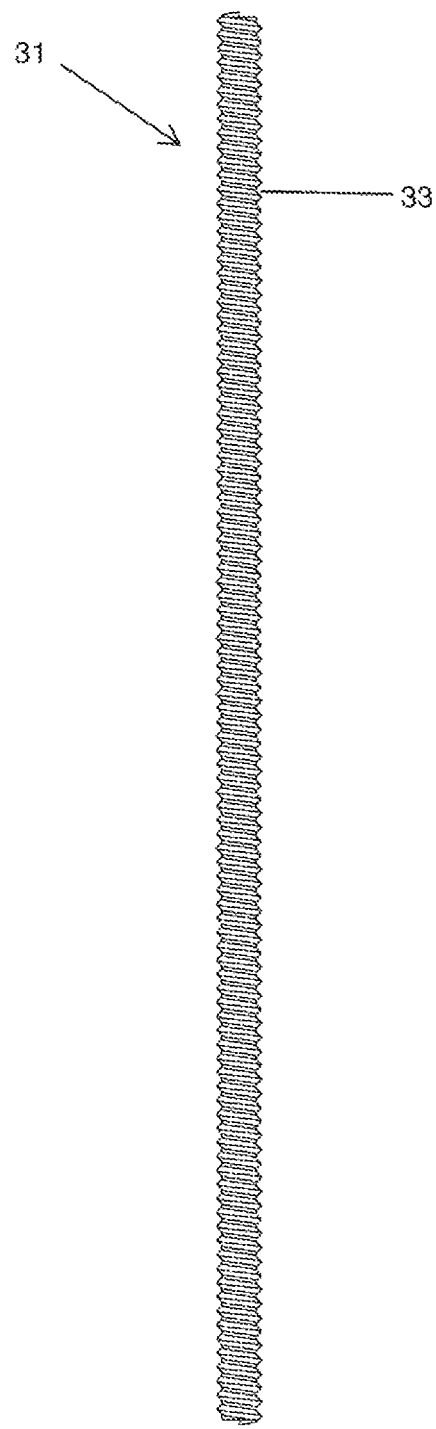
FIG. 5B illustrates a side view of the motor unit inner tubular member of FIG. 5A.
Figure 5A:
FIG. 5A illustrates a side cross sectional view of the motor unit inner tubular member.
Figure 6B:
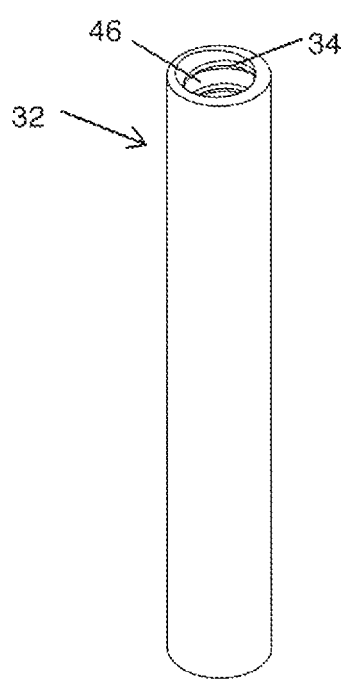
FIG. 6B illustrates a perspective view of the motor unit outer tubular member of 6A.
Figure 6A:
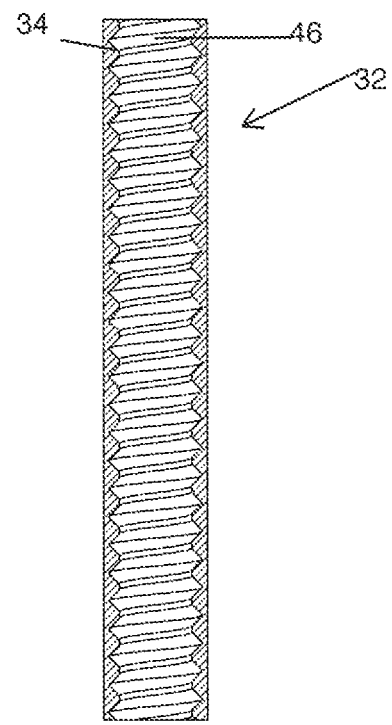
FIG. 6A illustrates a side cross sectional view of the motor unit outer tubular member.

FIGS. 5A and 5B illustrate a motor unit inner tubular member 31 and FIGS. 6A, 6B, 7A and 7B illustrate a motor unit outer tubule member 32 that fits over the motor unit inner tubular member 31. An assembled motor unit 130 illustrating an electric motor 36, inner and outer motor unit tubular members 31, 32, attached to the main body 100 of the device is illustrated in FIGS. 8A and 8B.

In a preferred embodiment, the inner tubular member of the motor unit 31 is between approximately 15 cm and 20 cm in length and disposed inside of the lumen 46 of the outer tubular member of the motor unit 32, which in turn, is around 5 to 7 cm. The luminal diameter of the motor unit inner tubular member 31 is approximately 0.5 mm to 1.0 mm larger than the diameter of the outer tubular member of the main body 100 so that the motor unit 130 can easily slide on the main body 100 as shown in FIGS. 7A and 7B. The outer surface 33 of the motor unit inner tubule member 31 is threaded in a helical configuration so that the so that the motor unit inner tubule member 31 can fit inside of the motor unit outer tubule member 32, which has a corresponding threaded inner surface 34 to fit the motor unit inner tubule member 31. The motor unit inner tubular member 31 can spin upwards or downwards within the outer tubular member 32. The threaded configuration of the motor unit tubule members 31, 32 converts part of the torque from an electric motor 36 into linear motion, thus facilitating the advancement of the distal end of the device through a CTO.

One embodiment of an electric motor has a gear system configured to generate oscillatory curvilinear torque motion in the rotor unit, which is attached to the main body 100. In one embodiment the rotor unit in turn transmits the curvilinear oscillatory motioning involving one third of a circle the main body 110 of the device. This pendulum-like motion of the main body 100, when transmitted to the proximal end of the main body 100 or drilling unit 21 will have less chance of plaque dislodgement and distal embolization when compared to the spinning movement. The motor unit 130 can be locked and unlocked with the main body via a locking screw device 35, preferably made from a polyethylene material, or the like.

Figure 9:
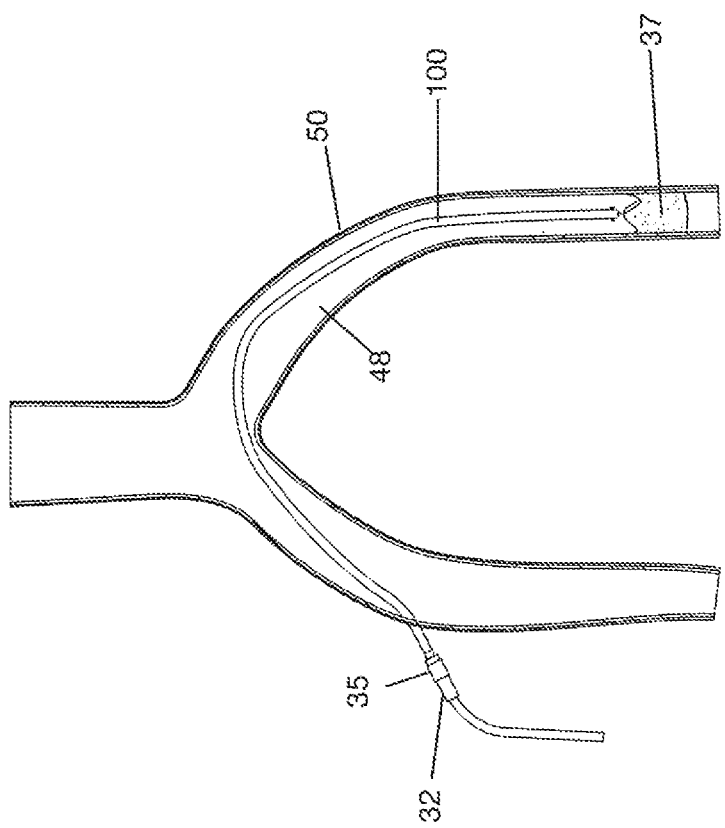
FIG. 9 is an exemplary view of a vascular drilling device inserted through a small hole in a patient's groin, the distal end of the vascular drilling device approaching an occlusion.

The electric motor 36 may be a DC or AC motor having a gear-box, the type being known by persons having skill in the art. In use, the operator inserts the main body 100 into the blood vessel through a small hole in the groin, and advances the distal end of the main body 100 adjacent to a CTO 37, as shown in exemplary form in FIG. 9. The motor unit 130 is inserted coaxially over the main body 100 and advanced near to the skin entry point of the main body 100. The motor unit inner tubular member 31 is then locked to the main body 100 using a lock screw member 35. Then the electric motor 36 is inserted coaxially over the main body 110, advanced, and locked to the distal end of the motor unit inner tubule member 31. The electric motor 36 is powered, and the operator guides the inward and outward movement of the locked-in combination of the motor unit inner tubule member 31 and main body 100. The torque created by the motor 36 and advancement of the inner tubular member 31 within the outer tubule member 32 transmits both linear and rotational movements to the distal end of the main body 100. In the embodiment of FIGS. 1A-E, the motor unit 130 transmits rotational movement to the entire main body 110, while in the embodiment depicted in FIG. 3A-D, the motor unit 130 is connected to the torque transmitting device 26, and only transmits rotational movement to the drilling unit 21.

Figure 10B:
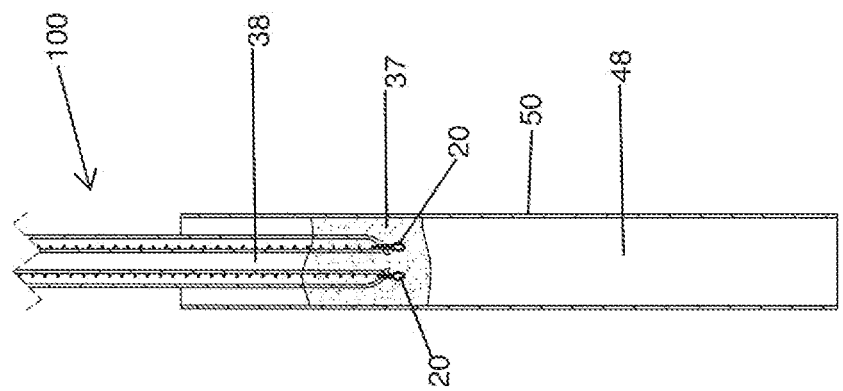
FIG. 10B is a side cross sectional view of the device of FIG. 1A within an occlusion.
Figure 10C:
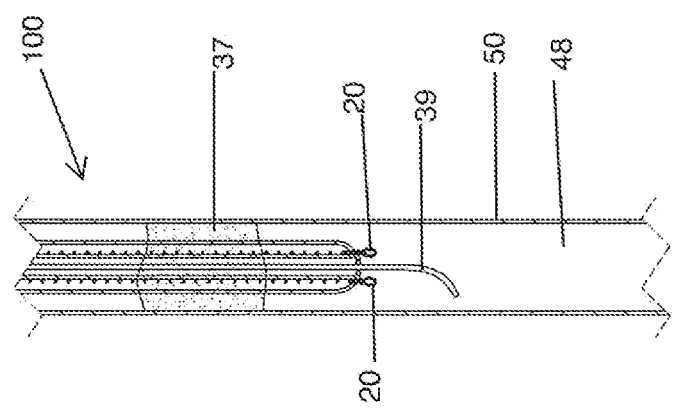
FIG. 10C is a front cross sectional view of the device of FIG. 1A after passing through an occlusion and after a guidewire has been inserted.

As the main body 100 or the drilling unit 21 spins, the wire loops 19, 20 in turn penetrate the proximal cap of the CTO and advances, as shown in FIGS. 10A-C. After successfully crossing the entire length of the occlusion 37, the operator confirms the intraluminal position of the distal end of the main body 100 injecting small amount of radiopaque contrast though the guidewire lumen under fluoroscopy guidance. Then the operator advances a guidewire 39 though the device lumen 38 into the vessel lumen 48 as shown in FIGS. 10C and 11.

In one embodiment of the device, the electric motor 36 rotates in a curvilinear oscillatory motion and does not comprise the inner and outer motor tubular members 31, 32. Here, the rotating axle of the electric motor 36 is attached directly to the torque transmitting device 25 and torque would transmit directly from the axle of the motor 36 to the drilling unit 21. In this embodiment, the operator gives linear motion to the main body 100 with an inward push as the motor 36 is providing the torque to the drilling unit 21 to fracture a CTO.

In the embodiment illustrated in FIGS. 8A and 8B, the operator locks the motor 36 to the torque transmitting device, advances the main body 100 gently into the blood vessel 48 and through the CTO 37 while the rotor unit of the electric motor 36 rotates the drilling unit in a curvilinear fashion via the torque transmitting device 26. Here, the operator adds the linear motion of the curvilinear movement of the advancing tip of the main body 100 and drilling unit 21 at the distal end of the main body 100. In this embodiment, the motor unit 130 is not used for linear motion as the operator controls the forward motion of the main body 100.

Figure 11:
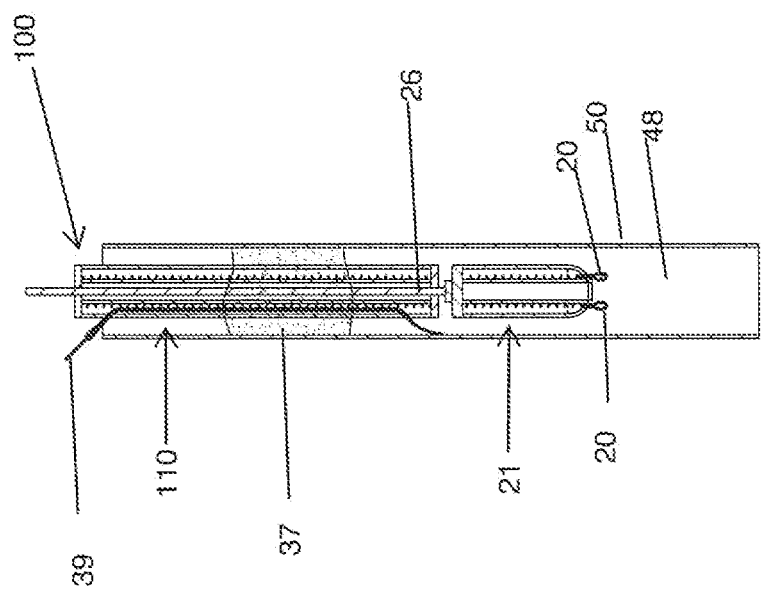
FIG. 11 is a front cross sectional view of the device of FIG. 3A after passing through an occlusion, and after a guidewire has been inserted.

FIG. 11 illustrates an exemplary embodiment of the device shown in FIGS. 3A-D inside of vessel 50 that has passed through a CTO 37. Here, the guidewire 39 exits the hole 29 located approximately 1 cm proximal to the distal end of the stationary unit 110. The guidewire 39 remains in the vessel lumen 48 after the main body 100 is pulled out from the patient. The guidewire 39 can then be used for further therapeutic interventions.

While all aspects of the present invention have been described with reference to the drawings, this description of various embodiments and methods shall not be construed in a limiting sense. The aforementioned is presented for purposes of illustration and description. It shall be understood that all aspects of the invention are not limited to the specific depictions, configures or relative proportions set forth herein which depend on a variety of conditions and variables. The actual dimensions and materials of a device constructed according to the principles of the present invention may obviously vary outside of the listed ranges and materials without departing from those basic principles. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications or variations of the described embodiments as falling within the true spirit and scope of the invention.

What is claimed:

1. A vascular drilling device for crossing an occluded blood vessel, said device having a main body comprising:
   an outer tubular member;
   an inner tubular member interposed within said outer tubular member, said outer and inner tubular members being configured for traversing a patient's vasculature and having a central hole for receiving a guidewire;
   a distal end cap secured to said outer tubular member and said inner tubular member;
   a plurality of distal end loops projecting in a distal direction from said distal end cap for fracturing an occlusion; and,
   a plurality of outer loops projecting radially outwardly from said outer tubular member,
   whereby said distal end loops and said outer loops fracture an occlusion within a blood vessel when said distal end loops and said outer loops are rotated and pushed through said occluded blood vessel.

2. The device of claim 1, wherein said plurality of distal end loops is a pair of distal end loops, and wherein said plurality of outer loops are a pair of outer loops substantially orthogonal in an axially aligned plane to said outer loops.

3. The device of claim 1, wherein said plurality of outer loops are positioned approximately between 0.5 cm and 1.0 cm from said distal end of said outer tubular member.

4. The device of claim 1 further comprising:
   at least one wire helical coil encircling said inner tubular member,
   whereby said helical coil improves the strength and flexibility of the said inner tubular member compared to the strength and flexibility of said inner tubular member without said at least one helical coil encircling said inner tubular member.

5. The device of claim 4, wherein said at least one wire helical coil has a hydrophilic polymer coating.

6. The device of claim 4, wherein said at least one wire helical coil are two wire helical coils.

7. The device of claim 4, wherein said plurality of distal loops and said plurality of outer loops are formed from said at least one wire helical coil.

8. The device of claim 1 further comprising
   an expandable balloon configured for inflation, said expandable balloon envelops at least a portion of said outer tubular member,
   whereby when said expandable balloon inflates, said expandable balloon dilates said occlusion and places said device in a vessel-centric position thereby substantially preventing unintended entry of said device into a subintimal plane of said blood vessel.

9. The device of claim 1, wherein said distal end cap is characterized by having a centrally positioned hole for guidewire exchange.

10. The device of claim 1, wherein said distal end cap is rounded.

11. The device of claim 1, wherein said device further comprises a motor unit.

12. The device of claim 11, further comprising:
   a motion sensor within said main body for measuring speed and character of rotation of said main body; and,
   a microprocessor for receiving and analyzing speed and feedback data;
   whereby said motion sensor and microprocessor, in conjunction with an operator's instructions, allow for better control of said device.

13. The device of claim 1, further comprising a guidewire tubular member disposed within said rotationally stationary unit for inserting a guidewire into a patient.

* * * * *